United States Patent [19]
Moses

[11] Patent Number: 5,387,178
[45] Date of Patent: Feb. 7, 1995

[54] MULTI-STIMULI CHAIR

[76] Inventor: Gary L. Moses, 440 Bledsoe Rd., NW., Albuquerque, N. Mex. 87107

[21] Appl. No.: 980,653

[22] Filed: Nov. 23, 1992

[51] Int. Cl.⁶ .......................................... A61M 21/00
[52] U.S. Cl. ...................................................... 600/27
[58] Field of Search ..................... 600/26–28, 600/9–15

[56] References Cited
U.S. PATENT DOCUMENTS

| | | | |
|---|---|---|---|
| 3,826,250 | 7/1974 | Adams | 600/28 |
| 4,893,615 | 1/1990 | Khabirova | 600/28 |
| 5,024,650 | 6/1991 | Hagiwara et al. | 600/26 |
| 5,047,006 | 9/1991 | Brandston et al. | 600/27 |

*Primary Examiner*—Lee S. Cohen
*Assistant Examiner*—John P. Lacyk
*Attorney, Agent, or Firm*—Deborah A. Peacock

[57] ABSTRACT

A multi-stimuli chair is provided for upright seated use. Stimuli, including light, color, sound, aroma, magnetic field, and vibration are provided by the chair to the user. The chair is compact, portable, and easily fittable through standard doorways.

46 Claims, 3 Drawing Sheets

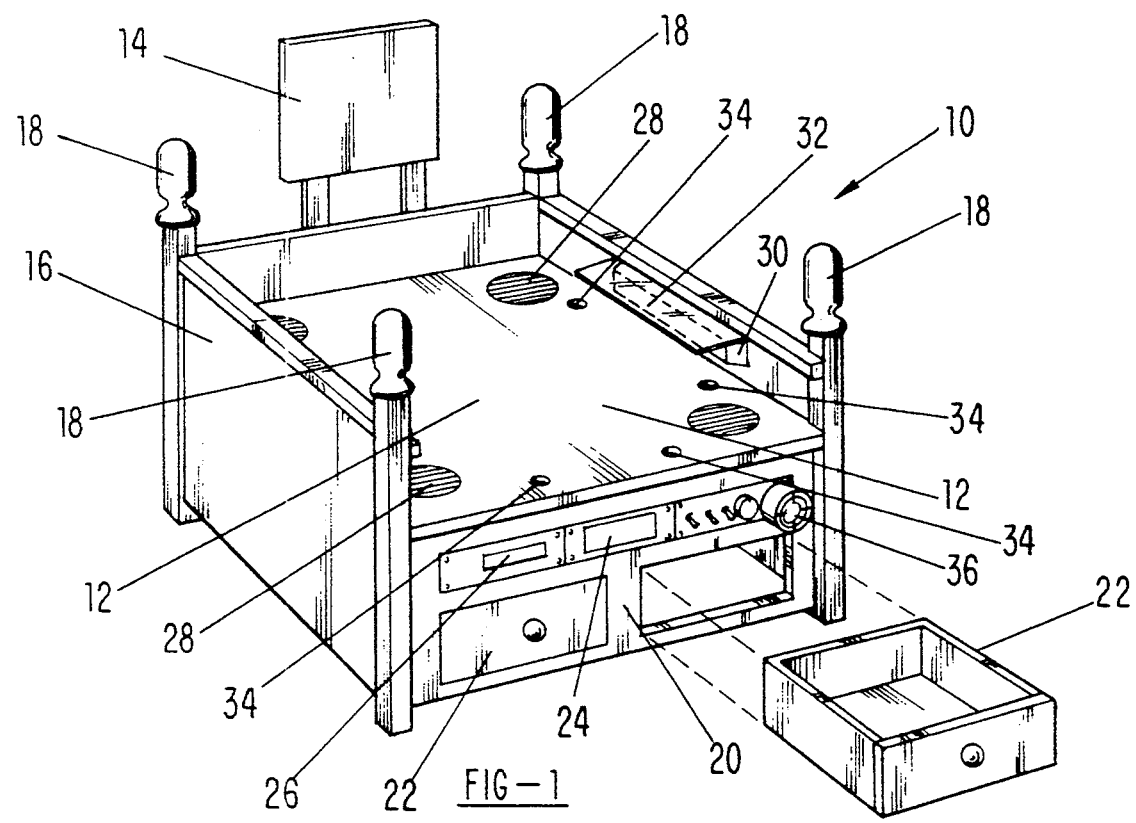
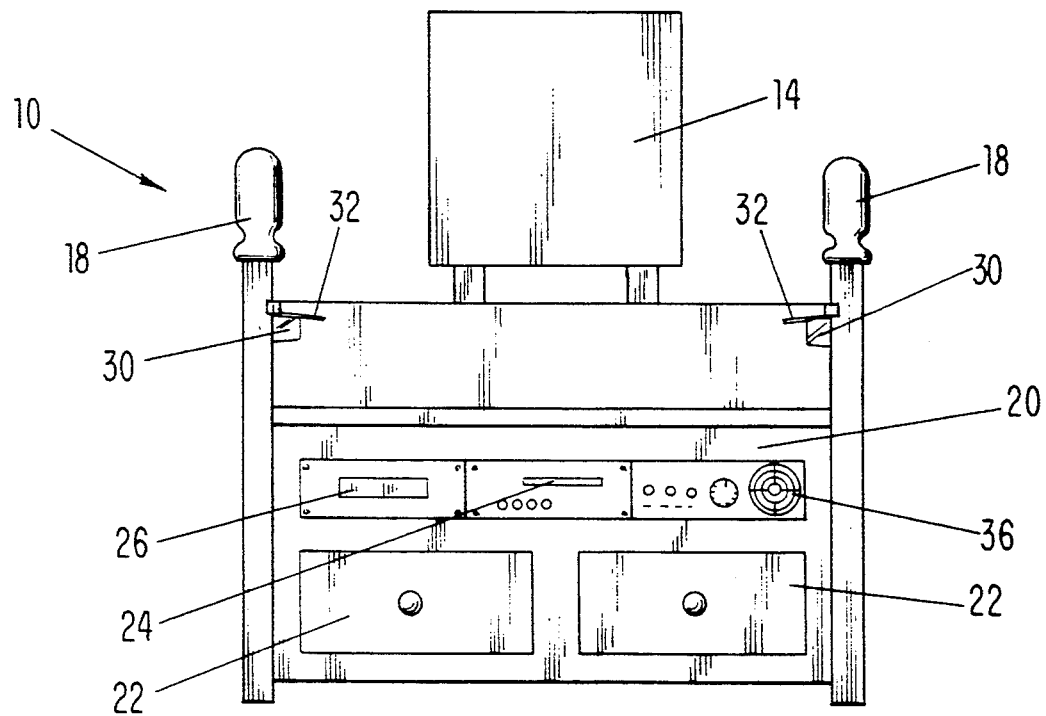

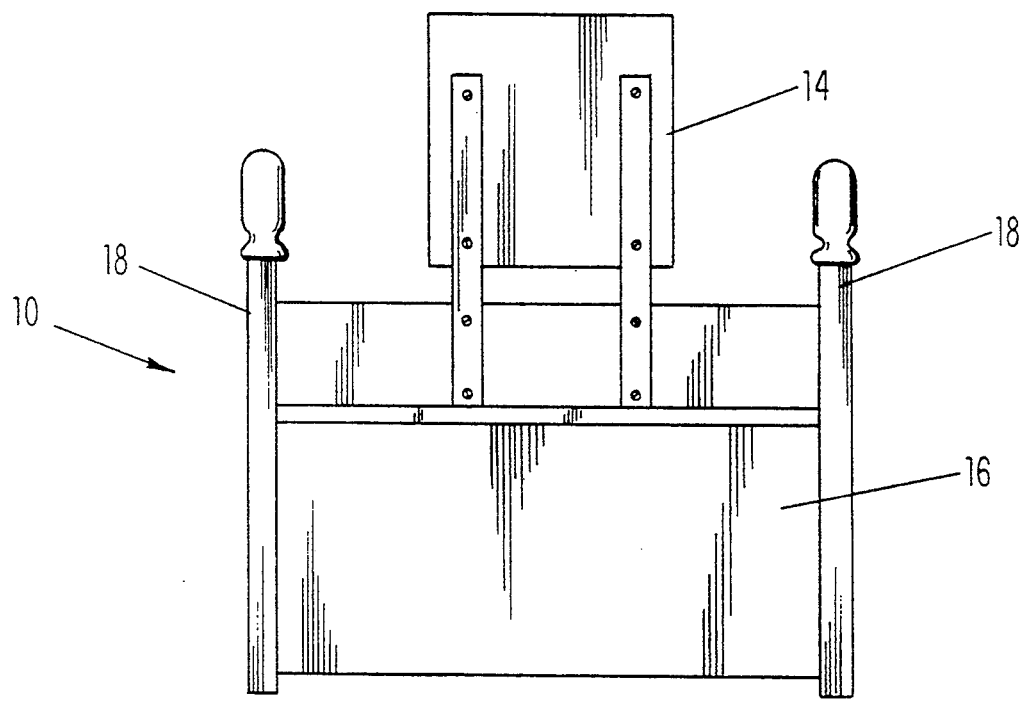
FIG — 5
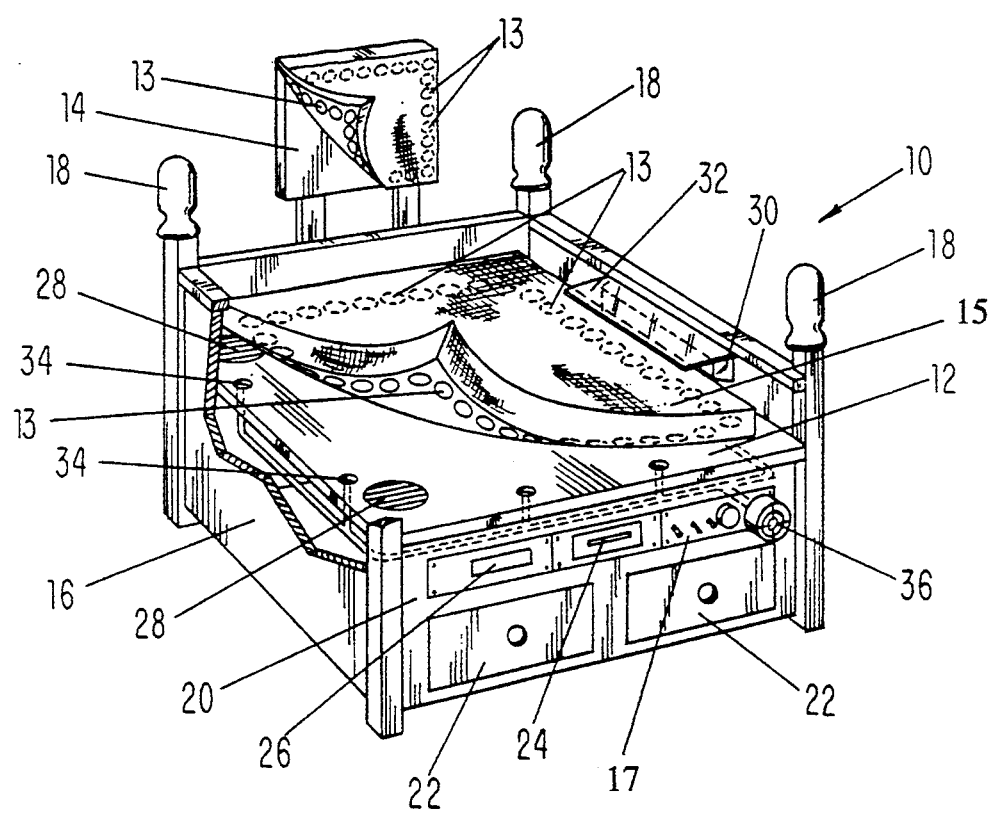
FIG — 6

MULTI-STIMULI CHAIR

BACKGROUND OF THE INVENTION

1. Field of the Invention. (Technical Field)

The present invention relates to a chair for creating or providing a multisensory or multistimulatory environment to a user. The user sits upright in the chair which provides sound, light, color, magnetic fields, and/or aroma or fragrance to create or produce a desired environment, such as relaxation, meditation, learning, energizing, therapeutic, creative, and the like.

2. Background Art

It has been found that sound, light, color, smell, magnetic fields and vibration can alter or enhance one's mood or environment to better allow for relaxation, meditation, learning, creative thinking, therapy, and the like. It is best, under many circumstances, to be seated to receive such stimuli.

Hagivara et al., U.S. Pat. No. 5,024,650, entitled Stress Dissolving Refreshment System, is representative of systems utilized in the prior art to create a relaxation state or environment for the user. The system requires the user to be in a reclining chair which is surrounded by a variety of stimuli. The '650 system is bulky, complex, and cannot be fittable or movable through a standard doorway. Although the '650 system provides several stimuli, it does not provide magnets (or a magnetic field) or variably colored lighting.

SUMMARY OF THE INVENTION

(Disclosure of the Invention)

The present invention is of a multi-stimuli chair, a method of providing predetermined sound, color and aromatic stimuli to a user.

The multi-stimuli chair and method of the invention comprises stationary seating for providing upright sitting by a user. Sound, light and fragrances are provided to the chair. A magnetic field may also be provided.

The chair comprises padding for providing upright and crossed leg sitting by the user. The chair may be in a flat, rectangular configuration.

In the preferred embodiment, the seat is disposed above a multiplicity of speakers for providing vibrations emitted from the speakers to the user when seated on the seat. A plurality of sound systems may be provided (e.g. cassette and compact disk (CD) players.

The chair may further comprise a timer for deactivating the sound, light, and/or aroma to the chair after a predetermined time.

Aromas or fragrances may be provided via perforated air flow conduit surrounding the seat.

The chair may further comprise storage (e.g. drawers) and a backrest. The chair is fittable through a standard doorway.

It is a primary object of the present invention to provide a chair, used for upright stationary seating, for relaxation, meditation, therapy, learning, creative thinking, and the like.

It is another object of the present invention to provide a multi-stimuli chair which is compact, portable, fittable through a standard door, easy to use, and inexpensive to manufacture.

Yet another object of the present invention is to provide multiple stimuli to a chair, such as sound, light, color, vibration, aroma and magnetic fields.

An advantage of the present invention is that a user can experience multiple stimuli in an upright seated posture.

Another advantage of the present invention is that the chair is portable, fittable through a standard doorway and positionable in a compact space.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIG. 1 is a perspective view of the preferred embodiment of the invention;

FIG. 2 is a front view of the FIG. 1 embodiment;

FIG. 5 is a back view of the FIG. 1 embodiment; and

FIG. 6 is a perspective view of the FIG. 1 embodiment showing pads with magnets embedded therein.

DESCRIPTION OF THE PREFERRED EMBODIMENTS

Figure 3:
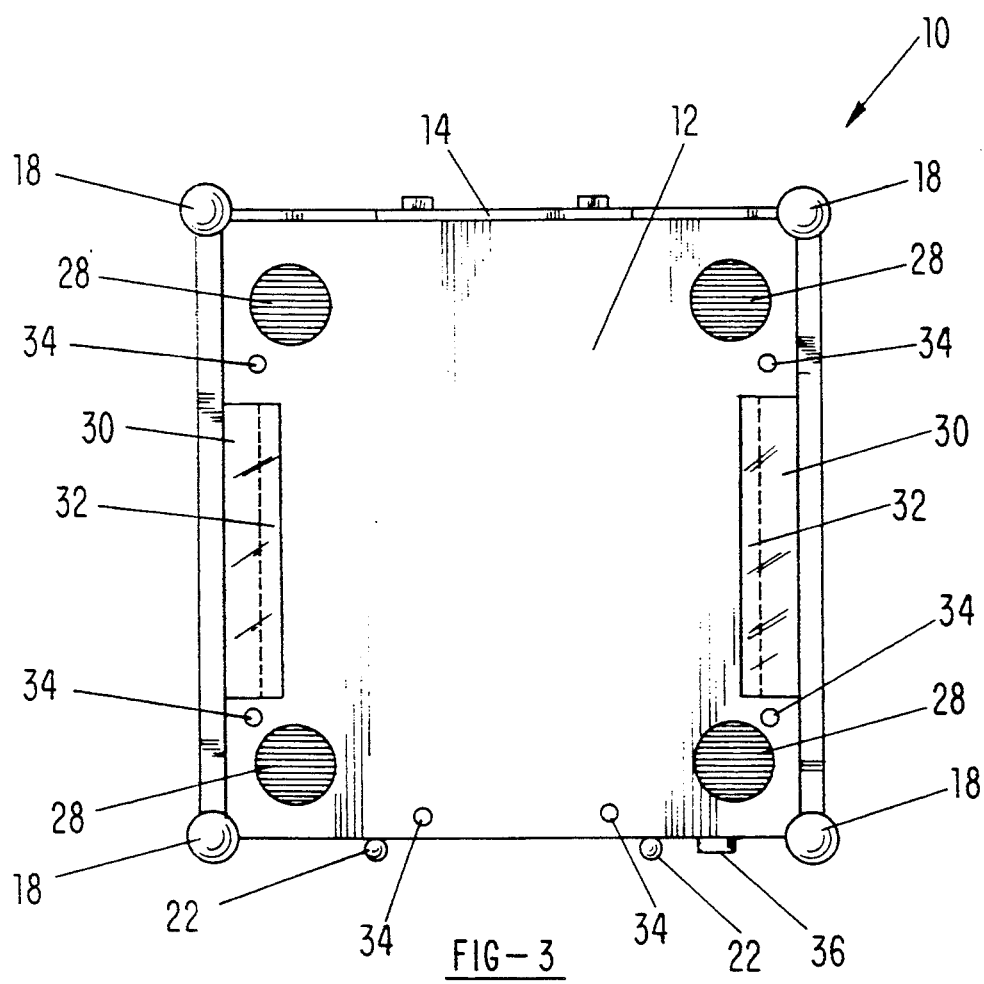
FIG. 3 is a top view of the FIG. 1 embodiment.
Figure 4:
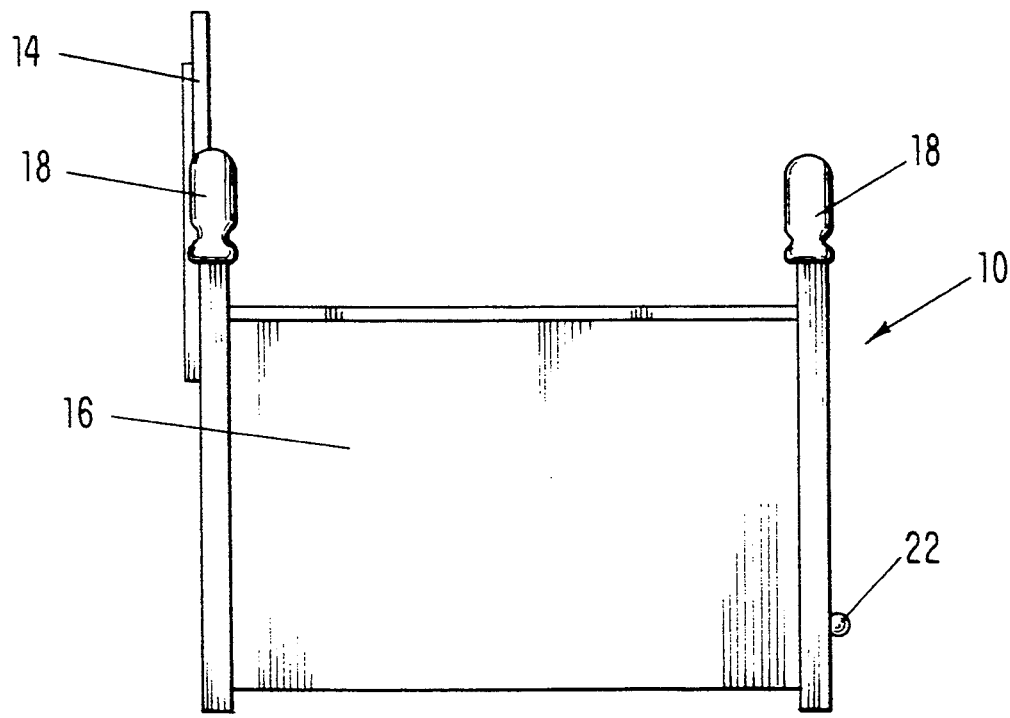
FIG. 4 is a side view of the FIG. 1 embodiment.

(Best Modes for Carrying Out the Invention)

The present invention relates to a chair for creating or providing a multisensory or multistimulatory environment to a user. The user sits upright in the chair which provides sound, light, color, magnetic fields, and/or aroma or fragrance to create or produce a desired environment, such as relaxation, meditation, learning, energizing, therapeutic, creative, and the like.

Reference is now made to the drawings which illustrate the preferred embodiment of the invention. Chair 10 comprises a rectangular or square framed configuration for upright, and preferably cross-legged seating by a user. Historically, the correct or best posture for thinking or meditation is in an upright sitting or "Lotus" position as compared to a standing or lying prone position. Chair 10 is compact and easily fittable through a standard doorway (e.g. typical house or office doorway) so that it can be readily moved.

Chair 10 comprises seat 12 with backrest 14. Seat 12 is padded 15 and contains magnets 13 embedded therein for providing a magnetic field. The magnets 13 are preferably made of natural carbon with the approximate gauss strength of the earth's electromagnetic field. Magnets 13 may also be provided to the backrest 14. The effect of magnets 13 is that they increase the tumbling effect of blood corpuscles, thereby improving circulation. This is a benefit to anyone who may sit for an extended time in meditation, and prevents numbness due to circulatory debility.

Chair 10 is framed 16 on all sides with a material such as wood. Decorative posts 18 may be disposed on the frame (e.g. at each corner). Front panel 20 (or additionally or alternatively other sides) has storage drawers 22 for storing sound recordings, fragrances, books, instructions, color transparencies, and the like. Front panel 20 further comprises controls 17 for lighting, sound, and a timer. The drawings illustrate both a CD (compact disk) 24 and radio cassette tape player 26, although other sound systems (e.g. DAT, phonorecords, 8-track tape-drives, and the like) may be utilized. Chair 10 is preferably equipped with a plurality of sound systems for user flexibility. Front panel 20 also provides for introduction 36 of preselected aromas or fragrances into chair 10.

Also in the preferred embodiment, the chair 10 further comprises varying colors of light to the chair. This may be accomplished by removably changeable colored transparencies 32 fittable over the light. The light is preferably adjacent to the seat 12 for providing upwardly directed light to the user.

Speakers 28 are preferably disposed beneath pad 15 and seat 12 (shown at four corners in the drawings) so that vibrations produced by the sound system can be felt by the user. For instance, if the user needs to feel energized, a fast beat music will not only be heard, but will also be felt, by the user. Similarly, relaxing words or music will be heard and felt as a relaxing vibration by the user. Other means for providing vibrations or movement to the chair or seat, in addition to the sound system may also be utilized in accordance with the invention. The term "sound" as used throughout the specification and claims is intended to include all such embodiments.

Lightbulbs 30 are disposed on the sides of chair 10 directly above padded seat 15. Color transparencies 32 may be placed over lightbulbs 30, depending on the color desired by the user. Alternatively, colored lightbulbs or lightbulbs with various color transparencies disposed thereon, can be controlled by on/off switches for each color desired. For instances, it is well known that red colors evoke a feeling of passion or power, whereas blue colors evoke a sense of security, etc. Modern psychology recognizes the connection of color to emotion. Public buildings such as football stadiums, hospitals, and convention centers are carefully painted with colors that are chosen for a specific desired effect. Likewise, such colors can be provided to the chair of the present invention. Even if the user's eyes are closed, light and colors from lightbulbs 30 and transparencies 32 will be sensed by the user, particularly because the user is seated upright, directly above lightbulbs 30 and color transparencies The user may choose to use no light, light, colored light, or a combination. Several colors or overlapping colors may also be used.

Air flow is introduced around chair via perforated conduit 34. Flowing air is provided via inlet through chamber 36. A variety of aromas or fragrances may be introduced to the air flow by adding drops to a cotton ball (not shown) in chamber 36. For instance, it is known that herbs or aromas provide various effects, such as relaxation, anti-inflammatory, analgesic, stimulant, astringent, etc.

In use, the user can select sound, fragrance, light, and air conditions in any combination for a desired effect. An automatic timer can shut off any or all of the stimuli at a preselected time or times. Standard wiring for the sound systems, lighting, timer and fan (for air flow) is utilized.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application are hereby incorporated by reference.

What is claimed is:

1. A multi-stimuli chair comprising:
   immobile seating means for providing upright sitting by a user further including magnets;
   means for providing sound to said chair;
   means for providing light to said chair; and
   means for providing aroma to said chair.

2. The chair of claim 1 wherein said seating means comprises padding means.

3. The chair of claim 1 wherein said seating means consists of a flat, rectangular configuration.

4. The chair of claim 1 wherein said seating means is disposed directly above said sound providing means for providing vibrations emitted from said sound providing means to the user when seated on said seating means.

5. The chair of claim 1 wherein said sound providing means comprises a multiplicity of speakers for surrounding the user when seated on said seating means.

6. The chair of claim 1 wherein said chair further comprises timer means for deactivating at least one stimuli selected from the group consisting of sound, light, and aroma after a predetermined time.

7. The chair of claim 6 wherein said sound providing means comprises a plurality of sound systems.

8. The chair of claim 1 further comprising color providing means for varying colors of light to said chair.

9. The chair of claim 8 wherein said color providing means comprises removably changeable colored transparencies disposed over said light providing means.

10. The chair of claim 1 wherein said light providing means is adjacent to said seating means for providing upwardly directed light to the user.

11. The chair of claim 1 wherein said aroma providing means comprises a perforated air flow conduit surrounding said seating means.

12. The chair of claim 1 wherein said seating means further comprise a storage area.

13. The chair of claim 12 wherein said storage area comprises at least one drawer.

14. The chair of claim 1 further comprising backrest means for the user to lean back against.

15. The chair of claim 1 wherein said seating means comprises padding.

16. A method of providing predetermined sound, color and aromatic stimuli to a user, comprising the steps of:
   a) placing a user in an immobile seat in an upright position and providing a magnetic field to the seat;
   b) providing predetermined sound to the user;
   c) providing predetermined colored light to the user; and
   d) providing predetermined aroma to the user.

17. The method of claim 16 wherein step b) comprises surrounding the user with a multiplicity of speakers when seated on the seat.

18. The method of claim 16 wherein step b) comprises surrounding the user with a multiplicity of speakers when seated on the seat.

19. The method of claim 16 further comprising the step of deactivating at least one stimuli selected from the group consisting of sound, light, and aroma after a predetermined time.

20. The method of claim 16 wherein light provided in step c) is provided adjacent to the seat for providing upwardly directed light to the user.

21. The method of claim 16 wherein the aroma provided by step d) is provided by a perforated air flow conduit surrounding the seat.

22. A multi-stimuli chair comprising:
   immobile seating means consisting of a flat, rectangular configuration for providing upright sitting by a user further including magnets;
   means for providing sound to said chair;
   means for providing light to said chair; and
   means for providing aroma to said chair.

23. The chair of claim 22 wherein said seating means is disposed directly above said sound providing means for providing vibrations emitted from said sound providing means to the user when seated on said seating means.

24. The chair of claim 22 wherein said sound providing means comprises a multiplicity of speakers for surrounding the user when seated on said seating means.

25. The chair of claim 22 wherein said chair further comprises timer means for deactivating at least one stimuli selected from the group consisting of sound, light, and aroma to said chair after a predetermined time.

26. The chair of claims 25 wherein said sound providing means comprises a plurality of sound systems.

27. The chair of claim 22 further comprising color providing means for varying colors of light to said chair.

28. The chair of claim 27 wherein said color providing means comprises removably changeable colored transparencies disposed over said light providing means.

29. The chair of claim 22 wherein said light providing means is adjacent to said seating means for providing upwardly directed light to the user.

30. The chair of claim 22 wherein said aroma providing means comprises a perforated air flow conduit surrounding said seating means.

31. The chair of claim 22 wherein said seating means further comprises a storage area.

32. The chair of claim 31 wherein said storage comprises at least one drawer.

33. The chair of claim 22 further comprising backrest means for the user to lean back against.

34. A multi-stimuli chair comprising:
   immobile seating means for providing upright sitting by a user;
   means for providing sound to said chair;
   means for providing light to said chair, further comprising color providing means for varying colors of light to said chair, said color providing means comprising removably changeable colored transparencies disposed over said light providing means; and
   means for providing aroma to said chair.

35. The chair of claim 34 herein said seating means comprises padding.

36. The chair of claim 34 wherein said seating means comprises magnets.

37. The chair of claim 34 wherein said seating means consists of a flat, rectangular configuration.

38. The chair of claim 34 wherein said seating means is disposed directly above said sound providing means for providing vibrations emitted from said sound providing means to the user when seated on said seating means.

39. The chair of claim 34 wherein said sound providing means comprises a multiplicity of speakers for surrounding the user when seated on said seating means.

40. The chair of claim 34 wherein said chair further comprises timer means for deactivating at least one stimuli selected from the group consisting of sound, light, and aroma to said chair after a predetermined time.

41. The chair of claim 38 wherein said sound providing means comprises a plurality of sound systems.

42. The chair of claim 38 wherein said light providing means is adjacent to said seating means for providing upwardly directed light to the user.

43. The chair of claim 34 wherein said aroma providing means comprises a perforated air flow conduit means surrounding said seating means.

44. The chair of claim 34 wherein said seating means further comprises a storage area.

45. The chair of claim 44 wherein said storage comprises at least one drawer.

46. The chair of claim 34 further comprising backrest means for the user to lean back against.

* * * * *